(12) United States Patent
Fan et al.

(10) Patent No.: US 10,743,814 B2
(45) Date of Patent: Aug. 18, 2020

(54) FAT FRACTION ESTIMATION USING ULTRASOUND WITH SHEAR WAVE PROPAGATION

(71) Applicants: Liexiang Fan, Sammamish, WA (US); John Benson, Issaquah, WA (US)

(72) Inventors: Liexiang Fan, Sammamish, WA (US); John Benson, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 849 days.

(21) Appl. No.: 14/020,643

(22) Filed: Sep. 6, 2013

(65) Prior Publication Data

US 2014/0276058 A1    Sep. 18, 2014

Related U.S. Application Data

(60) Provisional application No. 61/799,616, filed on Mar. 15, 2013.

(51) Int. Cl.
| | | |
|---|---|---|
| *A61B 5/00* | (2006.01) | |
| *A61B 8/08* | (2006.01) | |
| *A61B 8/14* | (2006.01) | |
| *A61B 8/00* | (2006.01) | |
| *G01S 7/52* | (2006.01) | |

(52) U.S. Cl.
CPC .......... *A61B 5/4872* (2013.01); *A61B 8/5223* (2013.01); *A61B 8/08* (2013.01); *A61B 8/14* (2013.01); *A61B 8/461* (2013.01); *A61B 8/469* (2013.01); *A61B 8/481* (2013.01); *A61B 8/485* (2013.01); *G01S 7/52022* (2013.01)

(58) Field of Classification Search
CPC .................................. A61B 8/08; A61B 8/485
See application file for complete search history.

(56) References Cited

U.S. PATENT DOCUMENTS

| | | | | |
|---|---|---|---|---|
| 4,621,645 | A | * | 11/1986 | Flax ................... G01S 7/52036 600/442 |
| 5,606,971 | A | | 3/1997 | Sarvazyan |
| 5,810,731 | A | * | 9/1998 | Sarvazyan ............... A61B 8/08 600/438 |
| 6,770,033 | B1 | * | 8/2004 | Fink ........................ A61B 8/08 600/443 |
| 8,118,744 | B2 | | 2/2012 | Palmeri |
| 8,961,418 | B2 | | 2/2015 | Fan |

(Continued)

FOREIGN PATENT DOCUMENTS

| | | |
|---|---|---|
| CN | 1343310 A | 4/2002 |
| CN | 102283679 A | 12/2011 |

(Continued)

OTHER PUBLICATIONS

Shen, (Precise Tracing of Impulsive Acoustic Radiation Force Induced Small displacements for Shear wave speed estimation, Ultrasonic Symposium 2011, IEEE, Oct. 18, 2011, pp. 2402-2407.*

(Continued)

*Primary Examiner* — Joseph M Santos Rodriguez

(57) ABSTRACT

Fat fraction is estimated from shear wave propagation. Acoustic radiation force is used to generate a shear wave in tissue of interest. The attenuation, center frequency, bandwidth or other non-velocity characteristic of the shear wave is calculated and used to estimate the fat fraction.

17 Claims, 3 Drawing Sheets

(56) References Cited

U.S. PATENT DOCUMENTS

| | | | |
|---|---|---|---|
| 2008/0249408 A1* | 10/2008 | Palmeri | A61B 8/08 600/438 |
| 2010/0016718 A1* | 1/2010 | Fan | A61B 8/00 600/438 |
| 2014/0316267 A1* | 10/2014 | Barry | A61B 8/085 600/438 |

FOREIGN PATENT DOCUMENTS

| | | | |
|---|---|---|---|
| CN | 102551801 A | 7/2012 | |
| WO | WO 2012-158877 | 11/2012 | |
| WO | WO 2012158877 | 11/2012 | |
| WO | WO 2013017105 | 2/2013 | |
| WO | WO 2013025798 A1 * | 2/2013 | A61B 8/085 |

OTHER PUBLICATIONS

C. T. Barry et al., "Shear Wave Dispersion Measures Liver Steatosis," Ultrasound in Med. & Biol., vol. 38, No. 2, pp. 175-182, 2012.

M. Sasso et al., "Controlled attenuation parameter (CAP): a novel VCTE™ guided ultrasonic attenuation measurement for the evaluation of hepatic steatosis: preliminary study and validation in a cohort of patients with chronic liver disease from various causes," Abstract, Ultrasound Med. Biol., vol. 36, No. 11, 2010.

French Search Report and Written Opinion dated Nov. 23, 2016 from counterpart French application No. 1452092, filed Mar. 13, 2014; 8 pages total.

Palmeri, Mark et al., "Noninvasive evaluation of hepatic fibrosis using acoustic radiation force-based shear stiffness in patients with nonalcoholic fatty liver disease", Journal of Hepatology, Elsevier, Amsterdam NL, vol. 55, No. 3, Dec. 9, 2010, pp. 666-672.

Nightingale, Kathryn, "Acoustic Radiation Force Impulse Imaging: Ex Vivo and In Vivo Demonstration of Transient Shear Wave Propagation," IEEE 2002, pp. 525-528.

Office Action dated Sep. 20, 2017 in corresponding Chinese application No. 201410096530.0.

* cited by examiner

FAT FRACTION ESTIMATION USING ULTRASOUND WITH SHEAR WAVE PROPAGATION

RELATED APPLICATIONS

The present patent document claims the benefit of the filing date under 35 U.S.C. § 119(e) of Provisional U.S. Patent Application Ser. No. 61/799,616, filed Mar. 15, 2013, which is hereby incorporated by reference.

BACKGROUND

The present embodiments relate to ultrasound imaging. In particular, the fat fraction in tissue is estimated using ultrasound. Nonalcoholic fatty liver disease (NAFLD) is the most common liver disease in American adults and children. NAFLD is characterized by excess hepatic fat accumulation as well as hepatic fibrosis. Magnetic resonance imaging (MRI) accurately measures the proton density fat fraction (PDFF) as a biomarker of hepatic fat content. However, MRI is not widely available and expensive. An ultrasound-based technique to quantify liver fat may advance clinical care.

BRIEF SUMMARY

By way of introduction, the preferred embodiments described below include methods, instructions, and systems for fat fraction estimation from shear wave propagation. Acoustic radiation force is used to generate a shear wave in tissue of interest. The attenuation, center frequency, bandwidth or other non-velocity characteristic of the shear wave is calculated and used to estimate the fat fraction.

In a first aspect, a method is provided for fat fraction estimation from shear wave propagation. An acoustic radiation force excitation is transmitted into a patient. Ultrasound is used to measure displacements at locations of tissue within a patient in response to a shear wave resulting from the acoustic radiation force excitation. A processor calculates attenuation of the shear wave from the displacements. The processor estimates fat fraction of the tissue as a function of the attenuation of the shear wave. An indication of the fat fraction is displayed.

In a second aspect, a non-transitory computer readable storage medium has stored therein data representing instructions executable by a programmed processor for fat fraction estimation from shear wave propagation. The storage medium includes instructions for generating acoustic radiation force focused at a location in tissue, measuring shear wave propagation resulting from the acoustic radiation force, calculating a property, other than velocity, of the shear wave propagation, and estimating the fat fraction for the tissue as a function of the property.

In a third aspect, a system is provided for fat fraction estimation from shear wave propagation. A transducer is configured to transmit an acoustic impulse excitation into a patient and is configured to scan with ultrasound a region of the patient. A receive beamformer is configured to generate data representing the region at different times after the acoustic impulse excitation. The data is generated from the scan with ultrasound. A processor is configured to estimate tissue displacement caused by a shear wave induced by the acoustic impulse excitation, to calculate an attenuation, center frequency, bandwidth, or combinations thereof of the tissue displacements, and to determine the fat fraction estimation from the attenuation, center frequency, bandwidth, or combinations thereof.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

One or more acoustic radiation force impulse (ARFI) induced shear wave propagation parameters are used to estimate fat fraction of tissue. Hepatic fat accumulation alters the propagation of shear waves in tissue. By measuring the difference in attenuation of the shear wave or frequency response (e.g., center frequency and/or bandwidth), an indication of the level or amount of fat accumulation is provided.

In the example below, the fat fraction is measured in a liver of the patient. The fat fraction is estimated to assist in diagnosis of NAFLD. In other embodiments, the fat fraction in a different tissue is measured.

Figure 1:
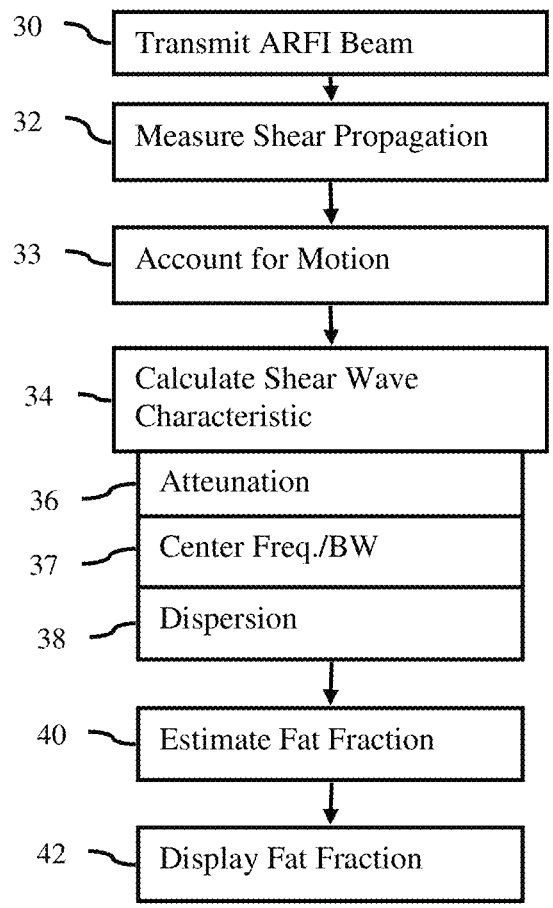
FIG. 1 is a flow chart diagram of one embodiment of a method for fat fraction estimation from shear wave propagation.

FIG. 1 shows a method for fat fraction estimation from shear wave propagation. The method is implemented by the system of FIG. 7 or a different system. Additional, different, or fewer acts may be provided. For example, acts 36, 37, and 38 represent examples. One, two, all three, or none of acts 36, 37, and 38 may be used. Other types of additional information may be used. As another example, act 42 is not performed. The estimated fat fraction is stored or transmitted rather than being displayed. The acts are performed in the order described or shown, but may be performed in other orders.

In act 30, an acoustic excitation is transmitted into a patient. The acoustic excitation acts as an impulse excitation for causing displacement. For example, a 400 cycle transmit waveform with power or peak amplitude levels similar or higher than B-mode transmissions for imaging tissue is transmitted as an acoustic beam. In one embodiment, the transmission is a shear wave generating sequence applied to the field of view. Any acoustic radiation force impulse (ARFI) or shear wave imaging sequence may be used.

The transmission is configured by power, amplitude, timing, or other characteristic to cause stress on tissue sufficient to displace the tissue at one or more locations. For example, a transmit focus of the beam is positioned near a bottom, center of the field of view or region of interest (ROI) to cause displacement throughout the field of view. The transmission may be repeated for different sub-regions or ROIs.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

The impulse excitation generates a shear wave at a spatial location. Where the excitation is sufficiently strong, a shear wave is generated. The shear wave propagates through tissue more slowly than the longitudinal wave propagates along the acoustic wave emission direction. This difference in timing is used to isolate the shear wave from a longitudinal wave, such as sampling at locations at certain times. The shear wave propagates various directions, including a direction perpendicular to the direction of the applied stress. The displacement of the shear waves is greater at locations closer to the location at which the shear wave is generated. As the shear wave travels longitudinally, the magnitude of the shear wave attenuates.

In act 32, a displacement response to the shear wave in the patient is detected. For example, the displacement profiles for two locations are demonstrated in FIG. 2. The excitation causes displacement of the tissue. A shear wave is generated and propagates from the focal region. As the shear wave travels through tissue, the tissue is displaced. Timing and/or lateral location are used to distinguish the shear wave from other generated waves. Longitudinal waves or other causes of displacement may be used instead of shear. The tissue is forced to move in the patient.

Figure 2:
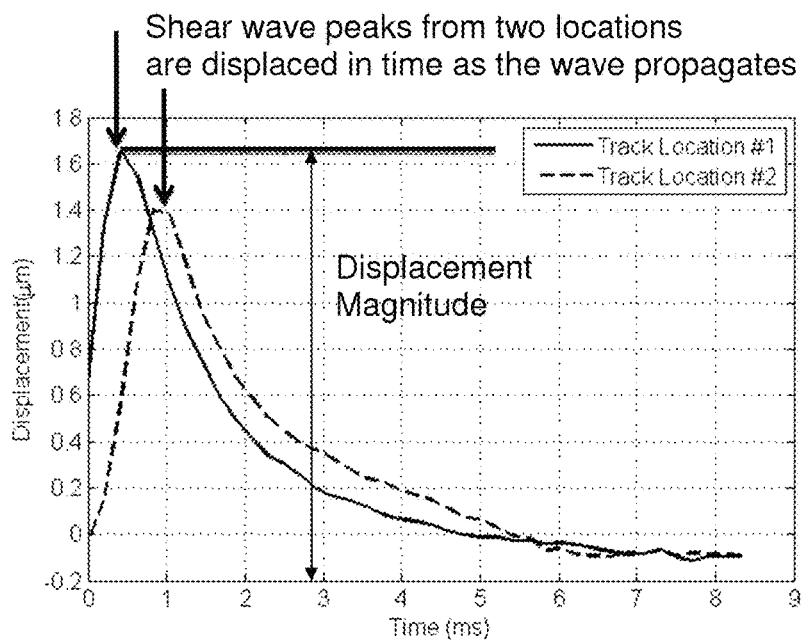
FIG. 2 is a graph showing two example displacements as a function of time.

The displacement caused by the force or stress is measured. The displacement is measured over time at one or more locations. The displacement measurement may begin before the stress or impulse ends, such as using a different frequency or coding. Alternatively, the displacement measurement begins after the impulse ends. Since the shear, longitudinal or other wave causing the displacement in tissue spaced from the point or region of stress takes time to travel, the displacement from a relaxed or partially stressed state to a maximum displacement and then to a relaxed state may be measured, as represented in FIG. 2. A temporal profile of displacement is determined. Alternatively, the displacement is measured only while the tissue is relaxing from the maximum.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. Ultrasound data is obtained. At least some of the ultrasound data is responsive to the shear wave. A region, such as a region of interest, entire field of view, or sub-region of interest, is scanned with ultrasound. The region is monitored to detect the shear wave. The region is any size, such as 5 mm in lateral and 10 mm in axial. For example, B-mode scans are performed to detect tissue displacement caused by the shear wave. Doppler, color flow, or other ultrasound mode may be used to monitor for the shear wave.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The monitoring is performed for any number of scan lines. For example, four or eight receive beams are formed in response to each transmission. After transmitting the excitation to generate the shear wave, B-mode transmissions are performed repetitively along a single transmit scan line and receptions along four or eight adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times. Some of the ultrasound data, such as at the beginning or end of the repetitions, may not be responsive to the shear wave.

As the shear wave propagates through the scan lines, the B-mode intensity may vary due to displacement of the tissue. For the monitored scan lines, a sequence of data is provided representing a time profile of tissue motion resulting from the shear wave. Echoes or reflections from the transmission are received. The echoes are beamformed, and the beamformed data represents one or more locations. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated as a function of time. For each depth or spatial location, a correlation over a plurality of depths or spatial locations (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations and/or rotations between the two data sets are performed.

The reference is a first set of data or data from another scan. The reference set is from before the ARFI pulse, but may be from after the ARFI pulse. The same reference is used for the entire displacement detection, or the reference data changes in an ongoing or moving window.

The correlation is one, two or three-dimensional. For example, correlation along a scan line away and toward the transducer or along a line perpendicular to the scan line is used. As another example, the translation is along two axes with or without rotation. In yet another example, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

FIG. 2 shows two example displacement profiles. The magnitude in distance of the motion vector over time from the reference data is shown. The period of analysis is over about 8 milliseconds, but may be longer or shorter (e.g., 12 milliseconds at a 4.8 kHz sample rate). Other displacement profiles are possible. Any number of locations may be measured for displacement, such as measuring every millimeter in the 10×5 mm region of interest. Displacement for each location and for each sample time is measured.

In act 33, motion of the transducer relative to the patient is accounted for in the measuring. The shear wave causes localized displacements in a region of interest. The region of interest is a sub-part of a larger field of view. The B-mode or other data from the larger field of view or just the entire region of interest may indicate motion caused by other sources than the shear wave. For example, breathing of the patient causes the patient or region of interest to shift relative to the transducer. As another example, voluntary motion by the patient or shifting of the transducer causes the region of interest to shift relative to the transducer.

By measuring motion as displacement of the region of interest and/or the larger field of view in one, two, or three-dimensions, the global motion is determined. The same data used for measuring shear wave displacement or data acquired by interleaved scans is used. The translation and/or rotation between times are determined. The locations represented by the data are shifted to counteract the global motion. This shift by selection of data, change of coordinates, or alteration of locations represents results in data from different times more likely representing the same tissue locations despite the global motion. Alternatively, the global displacement is subtracted from each of the local or location specific measures of displacement.

In act 34, one or more shear wave characteristics are calculated. Shear wave characteristics include various possible parameters or properties, such as velocity, attenuation, center frequency, or bandwidth. In one embodiment, the characteristic is other than velocity. Acts 36, 37, and 38 represent some example characteristics. Only one type, two types, all three types, or different types of characteristics are calculated.

A processor performs the calculation. The displacement information is used to determine the property without user input. Once the displacements are acquired, the processor automatically calculates the property for each location and/or time.

The shear wave property is detected from the displacements. The displacements over time and/or space are used. In one embodiment, the displacements for different depths are combined, leaving displacements spaced in azimuth or along the propagation direction of the shear wave. For example, the displacements for a given scan line or lateral location are averaged over depth. Alternatively to averaging, a maximum or other selection criterion is used to determine the displacement for a given lateral location.

In act 36, an attenuation property of the shear wave propagation is calculated from the displacements. The maximum displacement over time for each location is found. The shear wave magnitudes (peak values) at multiple locations along the propagation direction are calculated and used to derive the attenuation. Other measures of attenuation may be used.

The magnitude of displacement caused by the shear wave is determined. The magnitude may be derived from the displacement profile over time, such as identifying a maximum displacement. The magnitude of the maximum displacement is determined. The maximum displacement is calculated from the displacement profile. The peak or highest amount of motion or magnitude of shift by the tissue along a line, within a plane, or within a volume is calculated for the peak. The smoothed or filtered displacement curve is used for the maximum calculation. In other embodiments, the raw or unfiltered displacement curve may be used. The maximum value over the entire or portion of the profile is identified or determined. In the example of FIG. 2, the maximum displacement of 1.45 micrometers occurs at about 0.9 milliseconds for one location, and the maximum displacement of 1.65 micrometers occurs at about 1.2 milliseconds for the other location. Alternatively, the magnitude may be from a given time based on a distance from the focal region to the monitored location.

The temporal profile for a given location indicates detection of the shear wave at that location. The profile is examined for a non-noise or single instance of variation. A peak in the profile, with or without temporal low pass filtering, indicates the passing of the shear wave front. The greatest displacement is selected, but the average, initial non-noise displacement, or other displacement statistic may be used to indicate the passing.

In other embodiments, the energy or power is calculated for each location and used to derive attenuation. The power of the displacement is the square of the magnitude. The energy of the displacement is the integral over time. The magnitude, energy and/or power of the displacement may be used.

Figure 3:
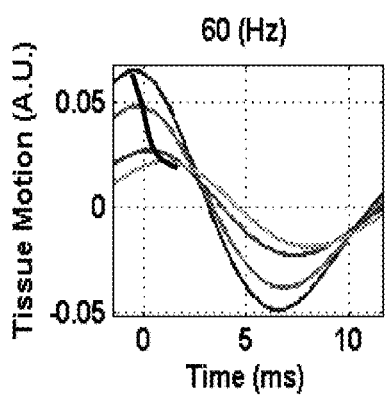
FIGS. 3 and 4 are graphs showing example attenuation calculations.
Figure 4:
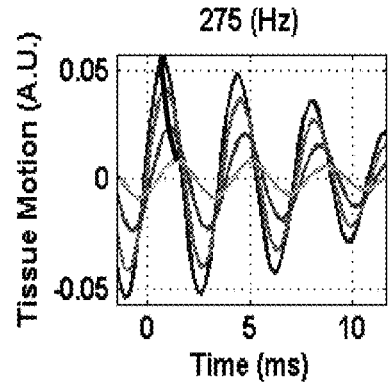

The attenuation is given by the slope of the maximums of the displacements over each of the locations. To calculate attenuation, ratios of adjacent maximum magnitudes are calculated. FIGS. 3 and 4 show an example line across the maxima of tissue motion for indicating attenuation for each of different narrow band components of the displacements. Each curve represents a detection position in the propagation direction. Alternatively, ratios of maximum magnitudes from non-adjacent (e.g., ratios from a reference to each of the locations) are calculated. The logs of the ratios provide the attenuations. An average attenuation over the azimuthally spaced locations may be used. Alternatively, the attenuation at each location is separately used. Other attenuation calculations may be used.

Figure 5:
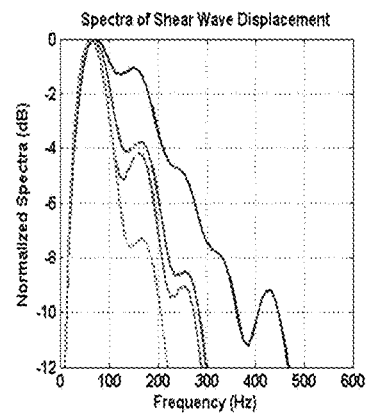
FIG. 5 is a graph of spectra for center frequency and/or bandwidth calculation.

In act 37, the center frequency, bandwidth, or center frequency and bandwidth of the displacements are calculated. These spectral characteristics are of the shear wave propagation as represented by displacements. For each location, a Fourier transform of the displacement as a function of time is determined. From the resulting spectrum, a center frequency and/or bandwidth is calculated. Any measure of center frequency or bandwidth may be used. For example, the center frequency is the frequency corresponding to peak value of power spectrum, and the bandwidth is the frequency range or difference over a range a 3 dB or other value down from the power spectrum peak or incorporating a value (e.g., $2/3$) of the area under the spectrum curve. FIG. 5 shows an example spectra with a horizontal line drawn for the 3 dB down location on one spectrum. The peaks are shown for center frequency. The center frequency can also be calculated as a mean or a weighted mean value in the frequency bandwidth range. Each spectra is of a detection position in the propagation direction.

The shear wave center frequency and/or bandwidth are provided for each location. The center frequencies and/or bandwidths may be used separately for each location. Alternatively, the center frequencies and/or bandwidths are combined for the ROI. For example, the average or median center frequency and bandwidth is calculated for the ROI. Other combinations may be used.

In act 38, the dispersion of the shear wave is calculated from the displacements. The dispersion is a measure of the velocity as a function of frequency. Any measure of dispersion may be used, such as a derivative of velocity as a function of frequency or slope of a line fit (e.g., linear regression fitting) to velocity as a function frequency.

Figure 6:
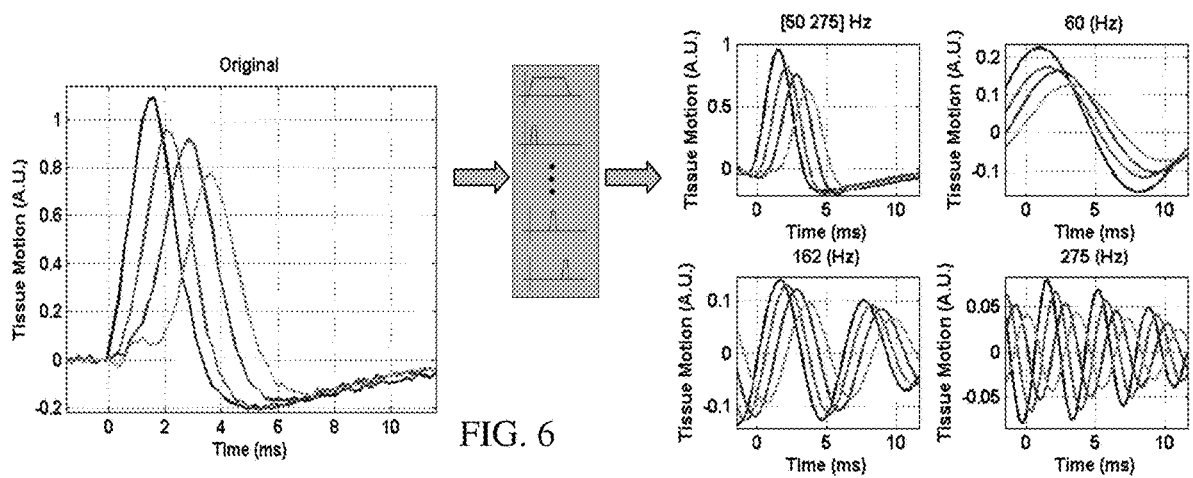
FIG. 6 illustrates example bank of filters applied to displacements.

In one embodiment, the displacement data is filtered as a function of time. The same data is filtered with different pass bands. For example, to obtain shear wave dispersion, a filter bank with ten or other number of center frequencies evenly distributed in a range, such as from 50 to 275 Hz, are applied to the shear wave displacement data. The filters are temporal filters, so the process is repeated separately for each location. FIG. 6 represents this filter bank approach where each curve represents a detection position in the propagation direction. In this example, each filter has a 32 Hz bandwidth with increments of 11.25 Hz between 50 Hz to 275 Hz using a 2nd order Elliptic filter with 0.5 dB ripple and 40 dB stop band attenuation. Other filters may be used.

The filtered displacement data for each passband is used to estimate the shear velocity. For example, the maximum filtered displacement indicates passing of the shear wave. For the location, the time or duration for the shear wave to travel from the origin (e.g., transmit focal region) to the location is determined. The maximum displacement or other part of the displacement profile indicates the time of arrival of the shear wave. Using the timing from generation of the shear wave to arrival, the travel time is calculated. The time is known from the relative time between generation and detection of the shear wave. The travel time may be non-linear.

The velocity of the shear wave is calculated from the timing information. The travel time is the inverse of the velocity. Using the distance and the travel time, the velocity is calculated. The distance is known from the scan line spacing (i.e., the transmit beam position for generating the shear wave and the receive beam position for detecting the shear wave).

Other techniques may be used to detect the peak in the profile and corresponding time and velocity. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

Since velocities are provided for different frequency bands, the dispersion of the shear velocity by frequency is provided. A derivative or other characteristic of this dispersion curve or line indicates the dispersion.

In act 40, the fat fraction is estimated for the tissue. The fat fraction is a function of the calculated property of the shear wave. Any function may be used. In one embodiment, an experimentally determined relationship between the property and fat fraction is used. Based on MRI-PDFF and/or liver biopsy measures, the actual value of the fat fraction in liver is determined. The relationship of ultrasound measured shear wave property (e.g., attenuation) to the actual fat fraction is determined. The relationship is used to determine the fat fraction based on the property in subsequent measures. In other embodiments, a theoretical or manually set function is used.

The processor calculates a value for the fat fraction for each location and/or for the ROI. Using a look-up table, the property is mapped to a value of the fat fraction. Other mapping may be used, such as calculating the fat fraction using the property in a curve representing the relationship. Statistics, machine-learnt function, fuzzy logic, or other mapping may be used.

Any of the properties may be used alone to estimate fat fraction. For example, attenuation is used to estimate fat fraction. Center frequency, bandwidth, or both are used to estimate fat fraction. Any characteristic of a curve or other measure may be used.

A combination of properties may be used. For example, the fat fraction estimated separately from two or more properties is averaged. As another example, the fat fraction mapping is a function of the two or more properties.

Other values than the fat fraction may be estimated. For example, the degree of fibrosis in liver is estimated. A velocity or characteristic of velocity as a function of location may indicate the amount of fibrosis. As another example, a combination of properties of the shear wave, such as velocity and attenuation, may be used to estimate fat and the degree of fibrosis. Both properties are used to estimate both fat and fibrosis. An iterative solution may be provided where fat and fibrosis are inter-related.

In act 42, an image of the fat fraction is generated. A value representing the estimated fat fraction is displayed on a screen. Alternatively or additionally, a graphic (e.g., curve or icon) representing the estimated fat fraction is displayed. Reference to a scale or other reference may be displayed. In other embodiments, the fat fraction as a function of location is displayed by color, brightness, hue, luminance, or other modulation of display values in a two-dimensional representation.

The fat fraction is indicated alone or with other shear wave information. For example, shear wave imaging is performed. The shear wave velocity, modulus or other information determined from tissue reaction to a shear wave is displayed. Any shear imaging may be used. The displayed image represents shear wave information for the region of interest or the entire imaging region. For example, where shear velocity values are determined for all of the grid points in a region of interest or field of view, the pixels of the display represent the shear wave velocities for that region. The display grid may be different from the scan grid and/or grid for which displacements are calculated.

The shear wave information is used for a color overlay or other modulation of display values. Color, brightness, luminance, hue, or other display characteristic is modulated as a function of the shear wave characteristic, such as the shear wave velocity. The image represents a two- or three-dimensional region of locations. The shear data is in a display format or may be scan converted into a display format. The shear data is color or gray scale data, but may be data prior to mapping with gray scale or color scale. The information may be mapped linearly or non-linearly to the display values.

The image may include other data. For example, shear wave information is displayed over or with B-mode information. B-mode or other data representing tissue, fluid, or contrast agents in the same region may be included, such as displaying B-mode data for any locations with shear wave velocity below a threshold or with poor quality. The other data assists the user in determining the location of the shear information. In other embodiments, the shear wave characteristic is displayed as an image without other data.

The additional fat fraction is displayed substantially simultaneously with the shear wave imaging. Substantially accounts for visual perception of the view. Displaying two images sequentially with sufficient frequency may allow the viewer to perceive the images as being displayed at a same time.

Any format for substantially simultaneous display may be used. In one example, the shear wave image is a two-dimensional image. The fat fraction is text, a graph, two-dimensional image, or other indicator of the values of the fat fraction estimate. A cursor or other location selection may be positioned relative to the shear image. The cursor indicates selection of a location associated with shear wave velocity information. For example, the user selects a pixel associated with an interior region of a lesion, cyst, inclusion, or other structure. The fat fraction for the selected location is then displayed as a value, a pointer along a scale, or other indication.

In another embodiment, shear wave and fat fraction images are displayed substantially simultaneously. For example, a dual-screen display is used. The shear wave image (e.g., shear wave velocity) is displayed in one area of the screen. The fat fraction as a function of location is displayed in another area of the screen. The user may view the different images on the screen for diagnosis. The additional information helps the user diagnosis the region.

Figure 7:
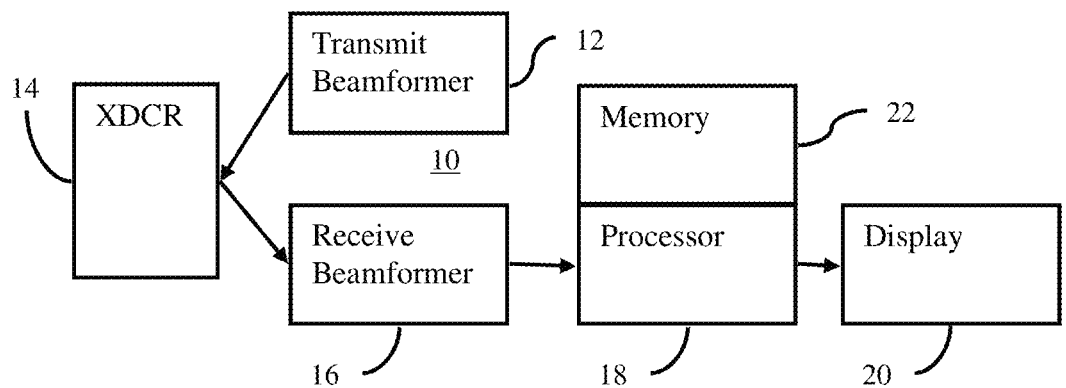
FIG. 7 is a block diagram of one embodiment of a system for fat fraction estimation from shear wave propagation.

FIG. 7 shows one embodiment of a system 10 for fat fraction estimation from shear wave propagation. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system.

The system 10 is a medical diagnostic ultrasound imaging system. In alternative embodiments, the system 10 is a personal computer, workstation, PACS station, or other arrangement at a same location or distributed over a network for real-time or post acquisition imaging.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans along the same line or lines is used. In Doppler imaging, the sequence may include multiple beams along a same scan line before scanning an adjacent scan line. For shear imaging, scan or frame interleaving may be used (i.e., scan the entire region before scanning again). Line or group of line interleaving may be used. In alternative embodiments, the transmit beamformer 12 generates a plane wave or diverging wave for more rapid scanning.

The same transmit beamformer 12 generates impulse excitations or electrical waveforms for generating acoustic energy to cause displacement. Electrical waveforms for acoustic radiation force impulses are generated. In alternative embodiments, a different transmit beamformer is provided for generating the impulse excitation. The transmit beamformer 12 causes the transducer 14 to generate pushing pulses or acoustic radiation force pulses.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time. A tracking pulse may be B-mode transmission, such as using 1-5 cycles. The tracking pulses are used to scan a region of a patient.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing locations along a plurality of lines at different times. By scanning the region of interest with ultrasound, data (e.g., beamformed samples) is generated. By repeating the scanning, ultrasound data representing the region at different times after the impulse excitation is acquired.

The receive beamformer 16 outputs beam summed data representing spatial locations. Data for a single location, locations along a line, locations for an area, or locations for a volume are output. Dynamic focusing may be provided.

The data may be for different purposes. For example, different scans are performed for B-mode or tissue data than for displacement. Alternatively, the B-mode data is also used to determine displacement. As another example, data for fat fraction estimation and shear imaging are acquired with a series of shared scans, and B-mode or Doppler scanning is performed separately or using some of the same data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, identifying magnitude of displacement, calculating travel time, calculating shear wave velocity, calculating one or more other properties of shear wave propagation, and/or estimating fat fraction. For example, the separate processor is configured by hardware and/or software to perform any combination of one or more of the acts shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation).

The processor 18 is configured to calculate a shear wave characteristic, such as the shear wave attenuation, center frequency, bandwidth, and/or dispersion. The attenuation, center frequency, bandwidth, or combinations thereof are calculated from the tissue displacements. For example, the attenuation is calculated from the slope of the distribution of a maximum magnitude of the shear wave along a propagation direction. The processor 18 is configured to find the maximum displacement of the displacement profile. In another example, the center frequency and the bandwidth are calculated from a spectrum of the tissue displacements over time for each of multiple locations. The processor 18 applies a Fourier transform to the displacements over time. In yet another example, a bank of filters or a memory and programmable filter may be implemented by or used with the processor 18 to determine a characteristic of the shear velocity as a function of frequency.

The processor 18 determines the fat fraction estimation from the attenuation, center frequency, bandwidth, other property of the shear wave, or combinations thereof. For example, the attenuation is used to look-up a fat fraction based on an empirically determined relationship. The attenuation may have about an 83-85% correlation with MRI-based measures of fat fraction. Similarly, the bandwidth may have about a 75% correlation with MRI-based measures of fat fraction. Greater or less correlations may be provided.

Shear wave velocity and/or modulus may additionally be calculated. For velocity, the maximum or other displacement is used to determine a travel time of the shear wave. The velocity is calculated using distance and the travel time. Velocity is determined for any number of locations.

The processor 18 is configured to generate one or more images. For example, a shear wave velocity image is generated. The shear wave velocity image is presented as an overlay or region of interest within a B-mode image. The shear wave velocity modulates the color at locations in the region of interest. Where the shear wave velocity is below a threshold, B-mode information may be displayed without modulation by the shear wave velocity.

Other information is included in the image or displayed sequentially or substantially simultaneously. For example, a fat fraction estimate image is displayed at a same time as the shear wave velocity. Each is generated as a color overlay in the region of interest in B-mode images. The velocity and fat fraction may be combined as a single overlay on one B-mode image. Alternatively, the fat fraction is displayed as text or a numerical value adjacent or overlaid on a B-mode or shear wave imaging image. The processor 18 may be configured to generate other displays. For example, the shear wave velocity image is displayed next to a graph, text, or graphical indicators of the fat fraction and/or degree of fibrosis. The information in addition to the shear wave velocity is presented for one or more locations of the region of interest without being in a separate two or three-dimensional representation.

The processor 18 operates pursuant to instructions stored in the memory 22 or another memory for fat fraction estimation from shear wave propagation. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The two dimensional images represent spatial distribution in an area. The three-dimensional representations are rendered from data representing spatial distribution in a volume. The display 20 is configured by the processor 18 or other device by input of the signals to be displayed as an image. The display 20 displays an image representing shear for different locations in a region of interest or an entire image. The display 20 displays fat fraction information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for fat fraction estimation from shear wave propagation, the method comprising:
   transmitting an acoustic radiation force excitation into a patient;
   measuring, with ultrasound, displacements at locations of tissue within a patient in response to a shear wave resulting from the acoustic radiation force excitation;
   calculating, by a processor, attenuation of the shear wave from the displacements, wherein calculating the attenuation of the shear wave comprises determining a maximum of the displacements over time for each of the locations and calculating a slope of the maximums of the displacements over the locations;
   calculating a center frequency, bandwidth, or center frequency and bandwidth of the displacements as a function of time;
   estimating, by the processor, fat fraction of the tissue as a mapping by a relationship stored in a look-up table, curve, statistic, or machine-learnt function, the mapping relating the attenuation of the shear wave and the center frequency, the bandwidth, or the center frequency and the bandwidth of the displacements as a function of time to the fat fraction by input of the attenuation of the shear wave and the center frequency, the bandwidth, or the center frequency and the bandwidth of the displacements to the look-up table, curve, statistic, or machine-learnt function, the look-up table, curve, statistic, or machine-learnt function outputting the fat fraction in response to the input; and
   displaying an indication of the fat fraction.

2. The method of claim 1 wherein measuring the displacements comprises repetitively scanning the locations with the ultrasound.

3. The method of claim 1 wherein estimating the fat fraction comprises looking up the fat fraction from a table indexed by the attenuation.

4. The method of claim 1 wherein measuring comprises measuring in a liver of the patient.

5. The method of claim 1 wherein displaying the indication comprises displaying a value of the fat fraction.

6. The method of claim 1 wherein displaying the indication comprises displaying an image representing the fat fraction at each of the locations.

7. A method for fat fraction estimation from shear wave propagation, the method comprising:
   transmitting an acoustic radiation force excitation into a patient;
   measuring, with ultrasound, displacements at locations of tissue within a patient in response to a shear wave resulting from the acoustic radiation force excitation;
   calculating, by a processor, a center frequency, bandwidth, or center frequency and bandwidth of the displacements as a function of time;
   estimating, by the processor, fat fraction of the tissue as a mapping of the center frequency, bandwidth, or center frequency and bandwidth of the displacements of the shear wave to the fat fraction using a stored look-up table, statistic, or machine-learnt function of a relationship of the fat fraction to the center frequency, bandwidth, or center frequency and bandwidth of the displacements of the shear wave; and
   displaying an indication of the fat fraction.

8. The method of claim 7 wherein calculating comprises calculating the center frequency, and wherein estimating comprise estimating as a function of the center frequency.

9. The method of claim 7 wherein calculating comprises calculating the bandwidth, and wherein estimating comprise estimating as a function of the bandwidth.

10. In a non-transitory computer readable storage medium having stored therein data representing instructions executable by a programmed processor for fat fraction estimation from shear wave propagation, the storage medium comprising instructions for:
    generating acoustic radiation force focused at a location in tissue;
    measuring shear wave propagation resulting from the acoustic radiation force;
    calculating a property as a center frequency of displacements or a bandwidth of displacements of the shear wave propagation; and
    estimating the fat fraction for the tissue from input of the property of the displacements to a look-up table storing a relationship of the property with the fat fraction.

11. The non-transitory computer readable storage medium of claim 10 wherein measuring the shear wave propagation comprises measuring displacement over time and at different locations.

12. The non-transitory computer readable storage medium of claim 10 wherein estimating the fat fraction comprises mapping the property to a value of the fat fraction.

13. The non-transitory computer readable storage medium of claim 10 further comprising accounting for motion of a transducer relative to the patient in the measuring.

14. A system for fat fraction estimation from shear wave propagation, the system comprising:
    a transducer configured to transmit an acoustic impulse excitation into a patient and configured to scan with ultrasound a region of the patient;
    a receive beamformer configured to generate data representing the region at different times after the acoustic impulse excitation, the data generated from the scan with ultrasound;
    a processor configured to estimate tissue displacement caused by a shear wave induced by the acoustic impulse excitation, to calculate a center frequency, a bandwidth, or combinations thereof of the tissue displacements, and to determine the fat fraction estimation from a look-up table-based mapping of the center frequency, bandwidth, or combinations thereof to the fat fraction.

15. The system of claim 14 wherein the processor is configured to calculate the center frequency and the bandwidth from a spectrum of the tissue displacements over time for each of multiple locations, and to determine the fat fraction estimation from the center frequencies and bandwidths at a single location or over the multiple locations.

16. The method of claim 7 wherein calculating comprises calculating from a Fourier transform of the displacements as a function of time.

17. The system of claim 14 wherein the processor is configured to calculate the center frequency, bandwidth, or combinations thereof from a Fourier transformer of the displacements as a function of time.

* * * * *